US006626799B2

(12) United States Patent
Watterson et al.

(10) Patent No.: US 6,626,799 B2
(45) Date of Patent: Sep. 30, 2003

(54) SYSTEM AND METHODS FOR PROVIDING AN IMPROVED EXERCISE DEVICE WITH MOTIVATIONAL PROGRAMMING

(75) Inventors: Scott R. Watterson, Logan, UT (US); William T. Dalebout, Logan, UT (US); Darren Ashby, Richmond, UT (US)

(73) Assignee: Icon IP, Inc., Logan, UT (US)

( * ) Notice: Subject to any disclaimer, the term of this patent is extended or adjusted under 35 U.S.C. 154(b) by 253 days.

(21) Appl. No.: 09/933,701

(22) Filed: Aug. 20, 2001

(65) Prior Publication Data

US 2002/0002103 A1 Jan. 3, 2002

Related U.S. Application Data

(63) Continuation of application No. 09/349,608, filed on Jul. 8, 1999.

(51) Int. Cl.⁷ .............................................. A63B 21/00
(52) U.S. Cl. ............................... 482/4; 482/8; 482/900
(58) Field of Search ........................ 482/1–9, 900–902; 434/247; 601/23

(56) References Cited

U.S. PATENT DOCUMENTS

| | | | |
|---|---|---|---|
| 3,518,985 A | 7/1970 | Quinton | |
| 3,602,502 A | 8/1971 | Hampl | |
| 4,151,988 A | 5/1979 | Nabinger | |
| 4,544,152 A | 10/1985 | Taitel | |
| 4,549,044 A | 10/1985 | Durham | |
| 4,659,074 A | 4/1987 | Taitel et al. | |
| 4,687,195 A | 8/1987 | Potts | |
| 4,828,257 A | 5/1989 | Dyer et al. | |
| 4,842,266 A | 6/1989 | Sweeney, Sr. et al. | |
| 4,848,737 A | 7/1989 | Ehrenfield | |
| 4,860,763 A | 8/1989 | Schminke | |
| 4,927,136 A | 5/1990 | Leask | |
| 4,959,713 A | 9/1990 | Morotomi et al. | |
| 4,998,725 A | 3/1991 | Watterson et al. | |
| 5,020,795 A | 6/1991 | Airy et al. | |
| 5,054,774 A | 10/1991 | Belsito | |
| 5,062,632 A | 11/1991 | Dalebout et al. | |
| 5,067,710 A | 11/1991 | Watterson et al. | |
| 5,078,152 A | 1/1992 | Bond et al. | |
| 5,086,385 A | 2/1992 | Launey et al. | |

(List continued on next page.)

OTHER PUBLICATIONS

*The FitLinxx Interactive Fitness Network* TM, *Integrated Fitness Corp.*, brochure, 1998.
Fitlinxx Interactive Fitness Network TM, *The Difference Between Surviving and Thriving May be as Simple as FitLinxx* TM, *Integrated Fitness Corp.*, brochure, 1998.
Forbes Digital Tool: Startups, *Sweat equity*, www.forbes.com, Feb. 1998.

(List continued on next page.)

*Primary Examiner*—Glenn E. Richman
(74) *Attorney, Agent, or Firm*—Workman Nydegger

(57) ABSTRACT

The present invention is directed to systems and methods for providing exercise devices with motivational programming. The programming includes motivational content and control signals, synchronized with the motivational content, for controlling operation of the exercise device. The motivational content preferably includes audio and/or video designed to simulate a group exercise setting and optionally instructional and educational content for the benefit of the user. The control signals can be carried in a carrier signals and can include bytes of data that define changes to the value of one or more operating parameters of an exercise device. The control signals can be audible to a listener and therefore act as an audible warning of upcoming changes in the one or more operating parameters of the exercise device.

45 Claims, 7 Drawing Sheets

U.S. PATENT DOCUMENTS

| | | | | |
|---|---|---|---|---|
| 5,104,120 | A | 4/1992 | Watterson et al. | |
| 5,113,427 | A | 5/1992 | Ryoichi et al. | |
| 5,145,475 | A | 9/1992 | Cares | |
| 5,149,084 | A | 9/1992 | Dalebout et al. | |
| 5,195,935 | A | 3/1993 | Fencel | |
| 5,213,555 | A | 5/1993 | Hood et al. | 482/57 |
| 5,308,296 | A | 5/1994 | Eckstein | |
| 5,313,942 | A | 5/1994 | Platzker | |
| 5,314,391 | A | 5/1994 | Potash et al. | |
| D348,493 | S | 7/1994 | Ashby | |
| 5,328,420 | A | 7/1994 | Allen | |
| 5,328,422 | A | 7/1994 | Nichols | |
| 5,352,166 | A | 10/1994 | Chang | |
| 5,382,209 | A | 1/1995 | Pasier et al. | 482/70 |
| 5,410,471 | A | 4/1995 | Alyfuku et al. | |
| 5,410,472 | A | 4/1995 | Anderson | |
| 5,433,679 | A | 7/1995 | Szymczak et al. | 482/54 |
| 5,462,051 | A | 10/1995 | Oka et al. | |
| 5,462,504 | A | 10/1995 | Trulaske et al. | 482/7 |
| 5,474,090 | A | 12/1995 | Begun et al. | |
| 5,489,249 | A | 2/1996 | Brewer et al. | 482/5 |
| 5,512,025 | A | 4/1996 | Dalebout et al. | 482/6 |
| 5,527,239 | A | 6/1996 | Abbondanza | 482/8 |
| 5,535,664 | A | 7/1996 | Rokowski | |
| 5,591,104 | A | 1/1997 | Andrus et al. | 482/7 |
| 5,600,310 | A | 2/1997 | Whipple, III et al. | |
| 5,619,412 | A | 4/1997 | Hapka | |
| 5,619,991 | A | 4/1997 | Sloane | |
| 5,626,539 | A | 5/1997 | Piaget et al. | 482/54 |
| 5,645,509 | A | 7/1997 | Brewer et al. | 482/4 |
| 5,697,834 | A | 12/1997 | Heumann et al. | |
| 5,702,323 | A | 12/1997 | Poulton | 482/8 |
| 5,720,771 | A | 2/1998 | Snell | |
| 5,722,418 | A | 3/1998 | Bro | |
| 5,738,612 | A | 4/1998 | Tsuda | 482/8 |
| 5,743,833 | A | 4/1998 | Watterson et al. | 482/54 |
| 5,749,372 | A * | 5/1998 | Allen et al. | 482/8 |
| 5,752,897 | A | 5/1998 | Skowronski et al. | 482/54 |
| 5,759,199 | A | 6/1998 | Snell et al. | |
| 5,779,596 | A | 7/1998 | Weber | 482/4 |
| 5,810,696 | A | 9/1998 | Webb | 482/52 |
| 5,836,770 | A | 11/1998 | Powers | 434/247 |
| 5,845,230 | A | 12/1998 | Lamberson | |
| 5,857,939 | A | 1/1999 | Kaufman | 482/8 |
| 5,865,733 | A | 2/1999 | Malinouskas et al. | |
| 5,873,369 | A | 2/1999 | Laniado et al. | |
| 5,880,677 | A | 3/1999 | Lestician | |
| 5,888,172 | A | 3/1999 | Andrus et al. | |
| 5,890,995 | A | 4/1999 | Bobick et al. | 482/4 |
| 5,905,442 | A | 5/1999 | Mosebrook et al. | |
| 5,911,132 | A | 6/1999 | Sloane | |
| 5,911,687 | A | 6/1999 | Sato et al. | |
| 5,917,405 | A | 6/1999 | Joao | |
| 5,929,748 | A | 7/1999 | Odinak | |
| 5,961,561 | A | 10/1999 | Wakefield, II | |
| 5,964,701 | A | 10/1999 | Asada et al. | |
| 5,967,975 | A | 10/1999 | Ridgeway | |
| 5,995,868 | A | 11/1999 | Dorfmeister et al. | |
| 5,997,476 | A | 12/1999 | Brown | |
| 6,010,451 | A | 1/2000 | Clawson | |
| 6,013,007 | A | 1/2000 | Root et al. | 482/8 |
| 6,014,432 | A | 1/2000 | Modney | |
| 6,033,344 | A | 3/2000 | Trulaske et al. | |
| 6,050,822 | A | 4/2000 | Faughn | 434/11 |
| 6,050,924 | A | 4/2000 | Shea | |
| 6,053,737 | A | 4/2000 | Babbitt et al. | 434/30 |
| 6,053,844 | A | 4/2000 | Clem | 482/8 |
| 6,059,692 | A | 5/2000 | Hickman | 482/8 |
| 6,106,297 | A | 8/2000 | Pollak et al. | |
| 6,132,337 | A | 10/2000 | Krupka et al. | 482/8 |
| 6,152,856 | A | 11/2000 | Studor et al. | 482/8 |
| 6,193,631 | B1 | 2/2001 | Hickman | 482/8 |
| 6,211,451 | B1 | 4/2001 | Tohgi et al. | 84/470 R |
| 6,231,481 | B1 | 5/2001 | Brock | 482/8 |
| 6,231,482 | B1 | 5/2001 | Thompson | 482/37 |
| 6,251,048 | B1 | 6/2001 | Kaufman | 482/8 |
| 6,312,363 | B1 | 11/2001 | Watterson et al. | 482/54 |
| 6,358,187 | B1 * | 3/2002 | Smith | 482/4 |
| 6,475,115 | B1 | 11/2002 | Candito et al. | 482/4 |
| 6,582,342 | B2 * | 6/2003 | Kaufman et al. | 482/8 |

OTHER PUBLICATIONS

Netpulse, *Networkingout—Coming Distractions: Netpulse Helps Exercisers Surf the Net at the Gym, Accomplish Serveral Goals at Once*, www.netpulse.com, Apr. 1998.

Netpulse, *Instead of having an equipment repair technician traveling over hill and dale, you may soon have equipment repaired via the internet*, www.netpulse.com, Jul. 1998.

Netpulse, *Infotech is supposed to make life easier–remember? Here's how to be sure it does.*, www.netpulse.com, Aug. 1998.

Netpulse, Exercise station connects to the Net, *Now you can sweat to the Net.*, www.netpulse.com, Sep. 1998.

Netpulse, New Fitness Equipment Combines Internet, Sweat, *Now you can surf and sweat*, www.netpulse.com, Jan. 1999.

Netpulse, Hop In, Log On and Sweat, *Netpulse exercise machines are the latest Web feat*, www.netpulse.com, Feb. 1999.

Netpulse ClubWatch TM, *Internet Powered Service*, brochure, Apr. 1999.

Netpulse, *State of the Art*, www.netpulse.com, Feb. 2000.

Netpulse, *Netpulse Files for Patents on its Pioneering Technology Inventions and Groundbreaking Business Methods in the Media and Fitness Markets*, www.netpulse.com, May 2000.

* cited by examiner

SYSTEM AND METHODS FOR PROVIDING AN IMPROVED EXERCISE DEVICE WITH MOTIVATIONAL PROGRAMMING

RELATED APPLICATION

This is a continuation application of U.S. patent application Ser. No. 09/349,608, filed Jul. 8, 1999, entitled "Systems and Methods for Providing an Improved Exercise Device with Motivational Programming," the disclosure of which is incorporated herein by this reference.

BACKGROUND OF THE INVENTION

This invention relates to exercise equipment and, more specifically, to systems and methods for providing improved exercise devices in combination with motivational programming.

In an attempt to improve their health and physical conditioning, consumers are purchasing home exercise devices in record quantities. One common problem with home exercise equipment is motivating the purchaser to use the device on a consistent and ongoing basis. In addition, many exercise devices involve repetitive actions, which can quickly become tedious and boring to a person exercising alone.

In recent years, health clubs have organized various exercise classes and routines involving a group setting. In the proper setting, a group approach to exercise creates a synergy, whereby individual members of the class derive encouragement and motivation from other members of the group. In addition, group settings promote a healthy sense of competition among group members. Initially, such group fitness and exercise classes typically involved aerobics, traditionally performed without the use of any ancillary exercise equipment or devices. In recent years, however, the group work out approach has been extended to classes that utilize various exercise devices. Take, for example, the recent rise in popularity of "Spinning Classes," in which each participant operates his or her own stationery exercise cycle in a group setting, with a coach or instructor leading the group through a prescribed program or routine. Similarly, with recent advances in the design of treadmills, it is possible to have "Treadmill Classes" wherein an instructor not only leads and motivates the group, but the instructor is also able to control the operation of the treadmills of all of the class participants from a single control panel.

One of the primary disadvantages with group training, however, is that it is typically available only at health clubs and, therefore, is not as convenient as exercising in the privacy and comfort of one's own home. It would, therefore, be a definite advancement in the art of home exercise equipment to provide the desirable benefits of group exercise by providing motivational, interactive programming that simulates a group exercise setting in the home.

Some efforts have been made in the prior art to introduce a level of "interactivity" into exercise machines. For example, U.S. Pat. No. 5,489,249 discloses a video exercise control system in which a video cassette recorder or similar device is coupled, via a hard wired connection, to an exercise machine, such as a treadmill, and wherein the speed and inclination of the treadmill are controlled by the VCR in synchronization with prerecorded audiovideo presentations. U.S. Pat. No. 5,645,509 discloses a remote exercise control system in which an exercise machine, such as a treadmill, which includes a control console that communicates via a communications module with an evaluation module located at a remote location. Signals indicative of the operating parameters of the treadmill are transmitted from the treadmill to the evaluation module, and control signals are transmitted from the remote evaluation module for controlling the operating parameters of the treadmill. U.S. Pat. No. 5,888,172 is representative of another approach found in the prior art, wherein an exercise device is coupled, via hard wired connection, to a video game device, such that the operating parameters of the exercise device are used as inputs to the video game controller, which then produces a motivational video display based on the inputs received. These approaches, however, do not facilitate live, interactive communications between a treadmill user at home and a trainer or coach in a remote location, which allow the trainer or coach to control the operating parameters of the user's treadmill on a real time basis.

BRIEF SUMMARY OF THE INVENTION

The present invention is directed to systems and methods for providing exercise devices with motivational programming. The present invention is particularly well suited to exercise devices that utilize one or more motors and/or other electrically driven actuators that control one or more operating parameters of the exercise device. The present invention contemplates the use of programming that includes motivational content and one or more control signals, synchronized with the motivational content, for controlling operation of the exercise device. The motivational content preferably includes audio and/or video designed to simulate a group exercise setting. In addition, the motivational content can include instructional and educational content for the benefit of the user. The programming can be live or prerecorded and can be broadcast over conventional broadcast channels, cable, satellite, the internet or any other means suitable for transmitting audio and/or video signals. Alternatively, the programming can be prerecorded and stored on a storage medium, such as audio cassette tapes, compact discs, mini-discs, videotapes, laser discs, digital video discs, computer diskettes or any other storage medium suitable for the storage and reproduction of audio and/or video signals. The present invention also includes means for reproducing the programming, including the motivational content along with the synchronized control signals. Finally, the present invention includes means for decoding the control signals and for controlling the operation of the exercise device in synchronization with the motivational content.

Accordingly, an object of the invention is to provide exercise devices that incorporate a standardized interface for receiving and decoding control signals embedded in multimedia (i.e., audio and/or video) programming for controlling various operating parameters of the exercise device in synchronization with the multimedia programming.

Another object of the present invention is to improve home exercise equipment by providing home exercise devices that are capable of simulating a group or class workout environment and synchronizing operation of the exercises devices with motivational programming.

Another object of the invention is to provide improved exercise devices, wherein programming containing motivational content and control signals can be reproduced using audio and/or video playback devices commonly found in the home, such as televisions, VCRs, home stereo equipment and the like, and the exercise device can decode and utilize the control signals to synchronize operation of the exercise device with the motivational content.

It is another object of the invention to provide exercise devices that are responsive to control signals that are encoded in programming external to the exercise device and containing audio and/or video and that can be transmitted and received by conventional broadcasting technologies.

Yet another object of the invention is to provide enhanced exercise devices, the operation of which can be controlled using interchangeable, multimedia programming containing motivational content and control signals that are synchronized with the motivational content.

Yet another object of the invention is to provide an improved exercise machine that facilitates live, interactive communications between a treadmill user at home and a trainer or coach in a remote location, and which allows the trainer or coach to control the operating parameters of the user's treadmill on a live, real time basis.

These advantages in addition to other objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention is directed to exercise devices that include one or more motors or other electrically driven actuators used to control one or more operating parameters of the exercise device. While the invention will be described in the context of a motorized treadmill, it should be understood that the invention is not limited to any particular type of exercise device. To the contrary, the present invention can be readily adapted to any motorized exercise device or any other exercise device that utilizes stepper motors, solenoids or any other electrically driven actuator to control any operating parameter of the device, such as speed, resistance, inclination or other similar operating parameters. As used herein, the term "exercise devices" shall refer broadly to any type of exercise machine, including, but not limited to, treadmills, exercise cycles, nordic style ski exercise devices, rowers, steppers, and elliptical or striding exercise devices.

Figure 1:
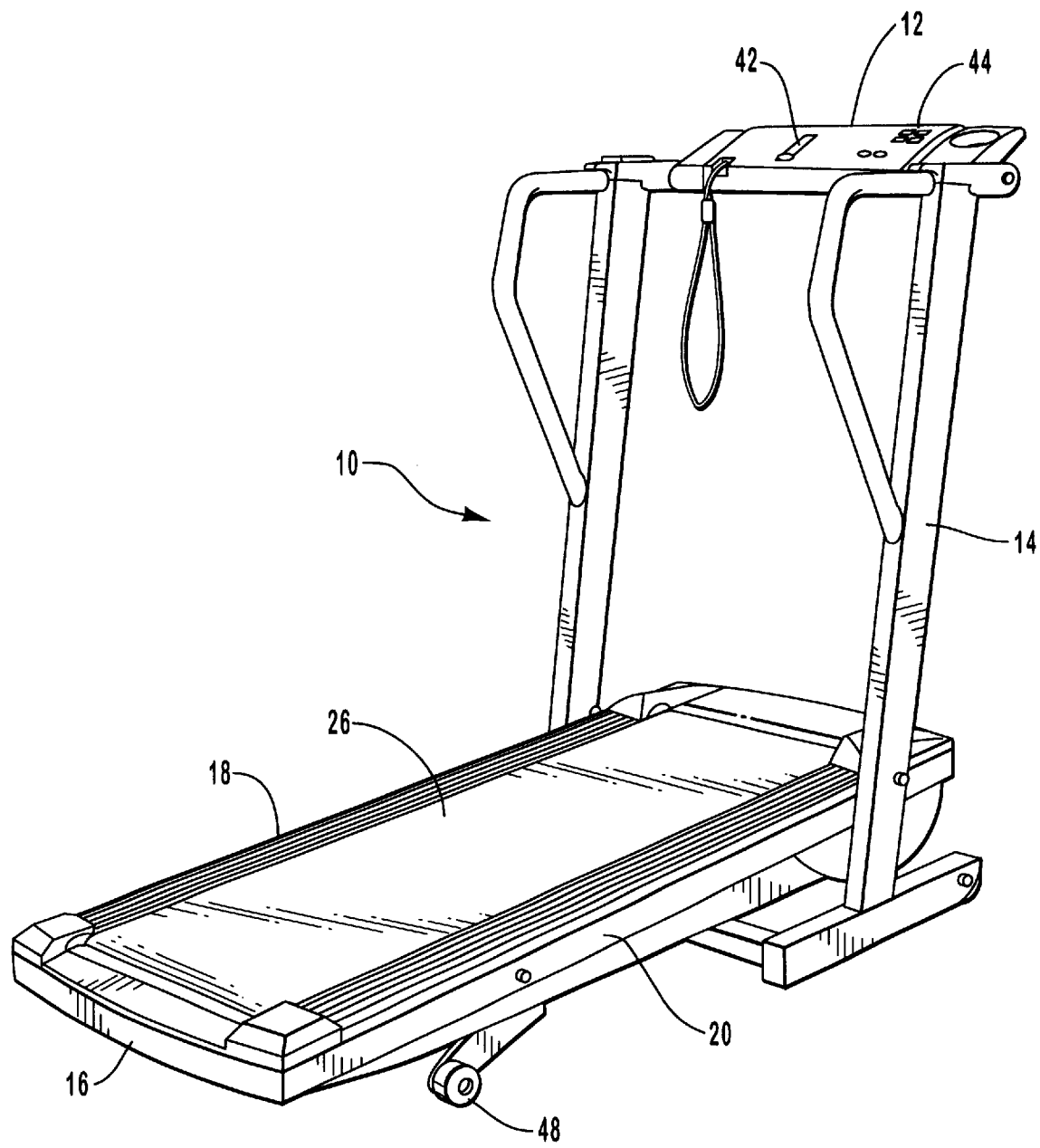
FIG. 1 is a perspective illustration of a reorienting treadmill with the tread base positioned in a first position for a user to perform exercises.
Figure 2:
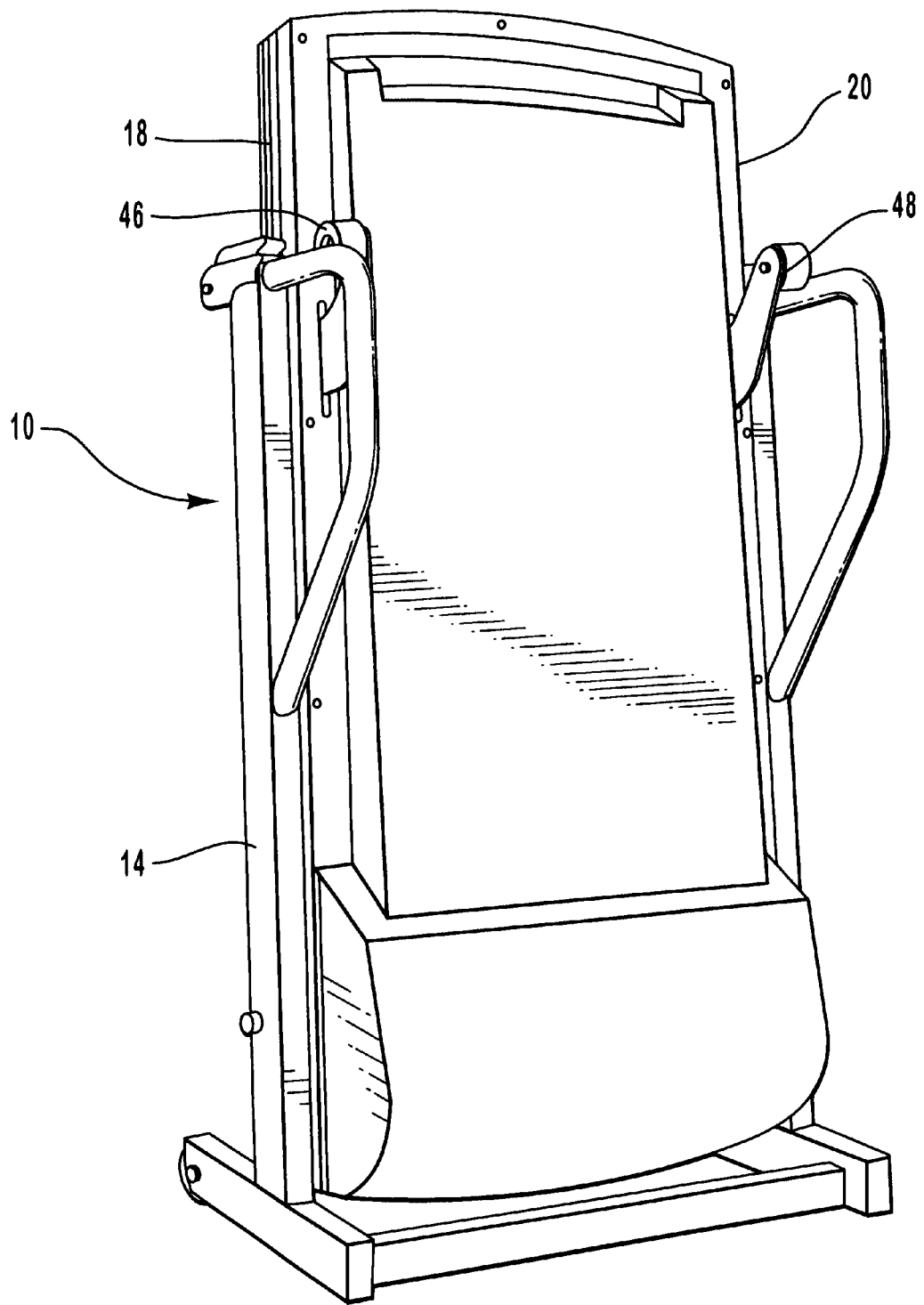
FIG. 2 is a perspective illustration of a reorienting treadmill with the tread base positioned in a second or storage position.
Figure 3:
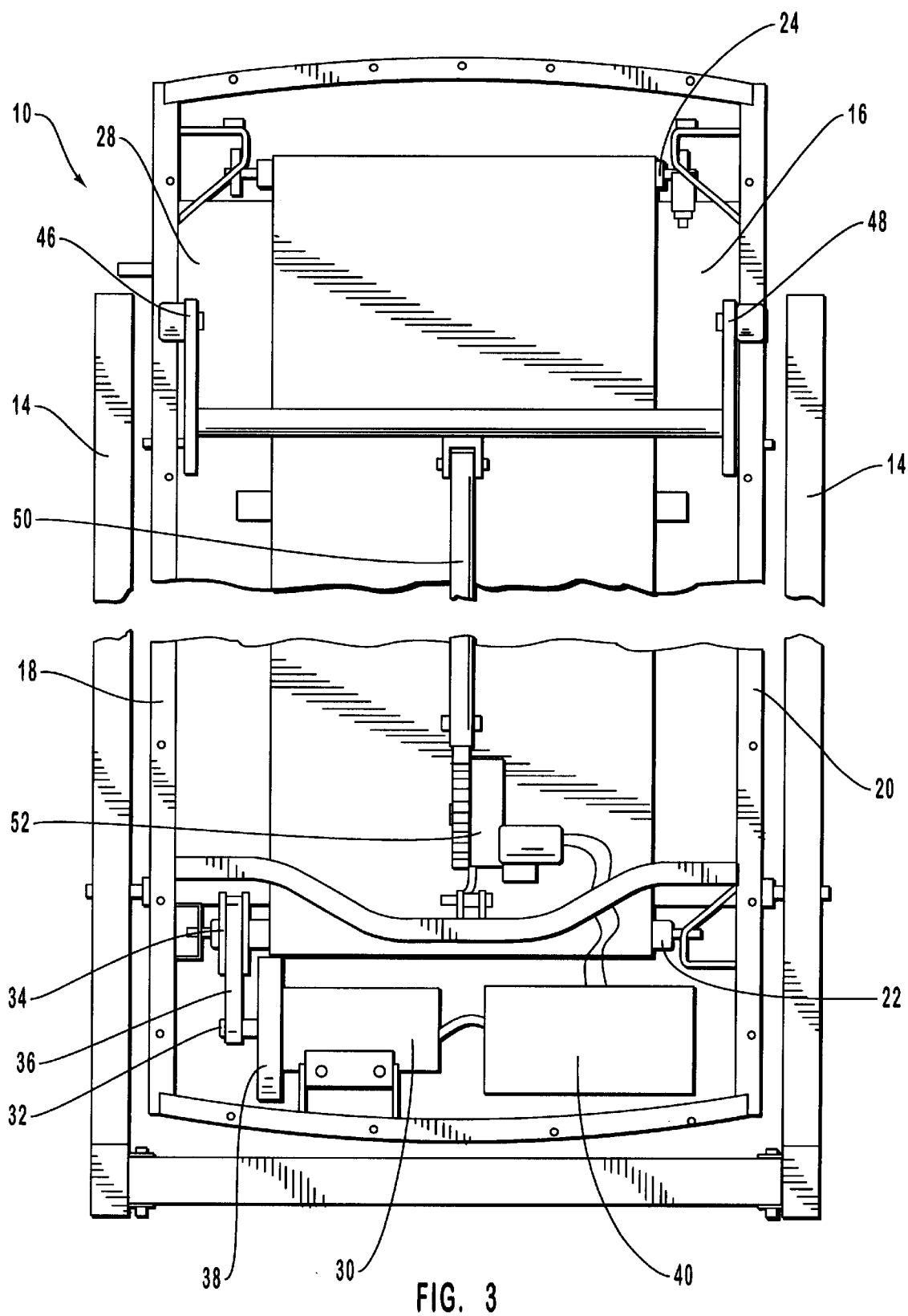
FIG. 3 is a partial plan view of portions of the reorienting treadmill illustrated in FIGS. 1 and 2 with the treadmill oriented in the second or storage position and with the bottom cover removed, revealing some of the internal components of the treadmill.

Referring now to FIGS. 1 through 4 generally, which depict a typical motorized, reorienting treadmill 10. Treadmill 10 includes a control panel 12 supported on a generally upright support structure 14 and a tread base 16. The tread base 16 typically consists of a pair of side rails 18 and 20, a front pulley 22 and a rear pulley 24 disposed between and supported by the side rails 18 and 20, and a continuous belt 26 extending between and around front and rear pulleys 22 and 24. A wooden deck 28 typically supports the upper run of belt 26. As best seen in FIG. 3, front pulley 22 is mechanically coupled to an electric tread drive motor 30 by means of pulleys 32 and 34 and a drive belt 36. Motor 30 also incorporates an inertial flywheel 38 and is electrically coupled to a treadmill controller 40. The operation of motor 30, and thus the speed of belt 26, is controlled by treadmill controller 40, either in response to direct input by the user through various input devices 42 (e.g., switches, rheostats, etc.) located on control panel 12 or in response to programming stored in nonvolatile memory incorporated into treadmill controller 40. Visual indicators relating to the operational status of treadmill 10, such as speed, inclination, duration of the work out, etc., are provided to the user through one or more output devices 44 located on control panel 12. Typical output devices 44 include LED displays and/or LCD displays.

Figure 4:
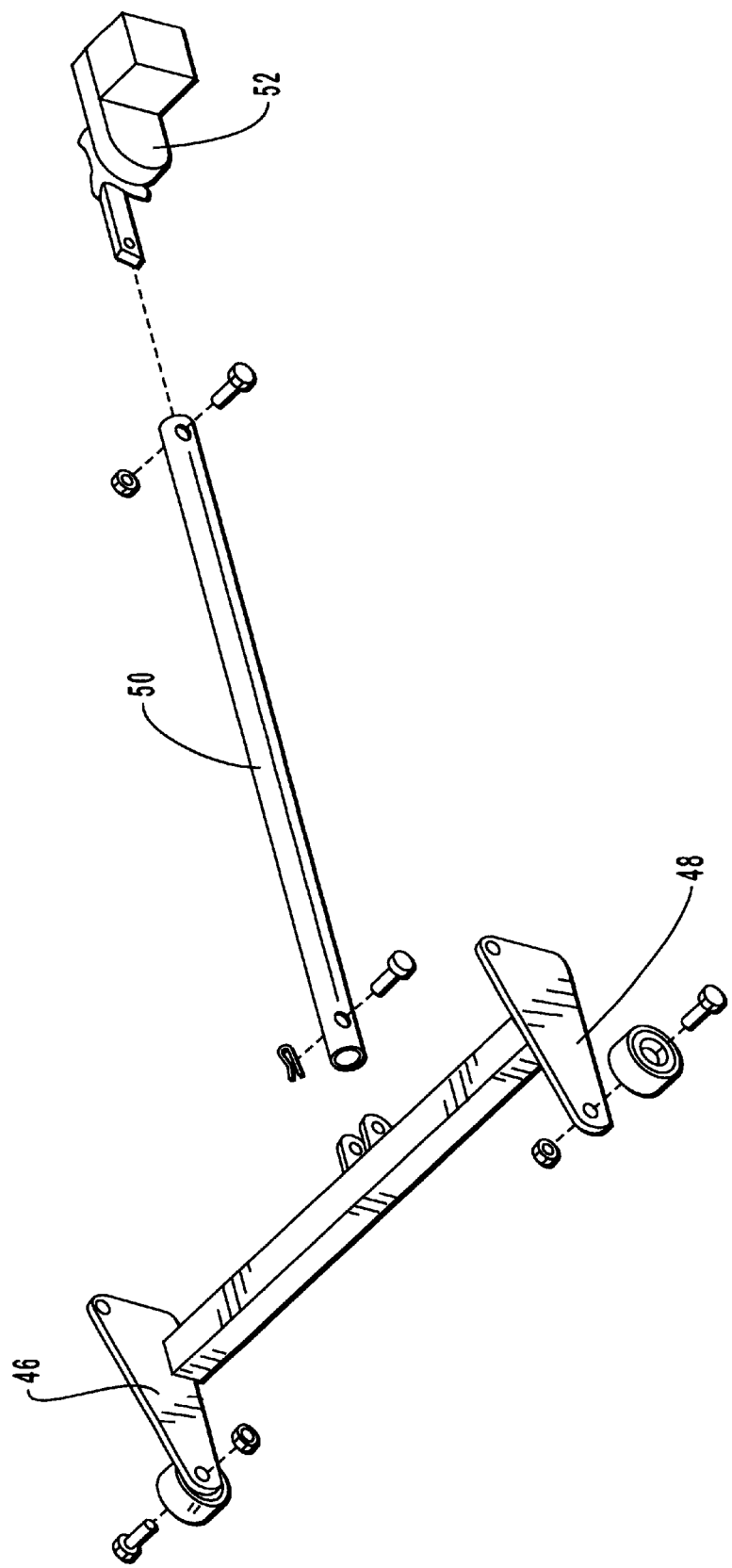
FIG. 4 is a partial exploded perspective view of the inclination mechanism incorporated into the treadmill illustrated in FIGS. 1 through 3.

In addition to the ability to control and vary the speed of belt 26, treadmill 10 also permits the degree of inclination of tread base 16 relative to the floor to be varied. Typically, this is accomplished through the use of an inclination drive motor that raises or lowers one end of tread base 16 relative to the other end. In the embodiment illustrated in FIGS. 1 through 4, a pair of rear feet 46 and 48 are rotatably attached to the rear of portion of side rails 18 and 20. As best seen in FIGS. 3 and 4, feet 46 and 48 are also mechanically coupled through a shaft 50 to an inclination drive motor 52, which causes feet 46 and 48 to pivot about their points of pivotal attachment to side rails 18 and 20, thereby selectively raising or lowering the rear end of tread base 16 relative to the front end thereof. Motor 52 is also electrically coupled to, and controlled by the treadmill controller 40, either in response to direct user input through the input devices 42 located on control panel 12 or to programming stored in nonvolatile memory incorporated into treadmill controller 40.

Again, neither the particular exercise device nor the particular design of a given exercise device is intended to limit the scope of the present invention. Rather, the present invention has broad application for any number of exercise devices.

In the present invention, programming is used that contains both motivational content and one or more control signals. The control signals are synchronized with the motivational content and are designed to control one or more operating parameters of the exercise device, such as treadmill 10, in synchronization with the motivational content of the programming. As used herein, the term "motivational content" is used to broadly refer to any audio material, including dialog, narration, sound effects and/or music, either alone or in combination with video material. In one presently preferred embodiment of the present invention, the motivational content consists of an audio/video presentation of a personal trainer and others engaged in a series of exercises of varying difficulty using treadmills. The motivational content includes voice-overs by the trainer, consisting of dialog designed to instruct and encourage the user of treadmill 10, and accompanying background music. The tone and tempo of both the dialog and the background music is selected to match the intensity of the workout. While the foregoing selections are provided by way of example, it should be understood that the selection of the particular audio and video used to motivate and inspire the user of treadmill 10 is virtually limitless and is left to the imagination of the producer of the motivational content.

As mentioned above, the programming also contains control signals for controlling one or more operational parameters of the exercise device. In the case of treadmill 10, the programming includes control signals that control the speed of belt 28, as well as signals that control the degree of inclination of tread base 16. Furthermore, the control signals are synchronized with the motivational programming such that the intensity of the operation of treadmill 10 coincides with the intensity of the motivational content of the programming, and vice versa.

The programming may be either performed live or prerecorded. Whether live or prerecorded, programming incorporating audio and video can be transmitted via existing broadcast technology, including television broadcast over the airwaves, via cable, via satellite, via telephone lines, via the internet or any other suitable transmission technology or medium. Similarly, programming containing only audio can be transmitted via existing radio broadcast technology, including over the airwaves, via cable, via satellite, via telephone lines, via the internet or any other suitable transmission technology or medium. In this way, the present invention is compatible with existing conventional broadcast technologies and can interface with existing audio and/or video components commonly found in homes, thereby reducing the overall cost of the exercise device.

The programming may also be prerecorded and stored on a suitable storage medium. Any form of storage medium that is suitable for storing audio and/or video signals or data can be used and is within the scope of the present invention. For example, programming that contains only audio can be stored on audio cassette tapes, compact discs (CDs), minidiscs (MDs), computer diskettes or any other storage media suitable for storing audio programming. Similarly, programming that contains both audio and video can be stored on videotapes, laser discs (LDs), digital video discs (DVDs), computer diskettes or any other storage media suitable for storing audiovideo programming.

The present invention also includes means for reproducing the programming. The particular reproducing means is selected based on either the manner in which the programming is transmitted (e.g., television or radio signals) or the storage media on which the programming is stored (e.g., tape player for audio tape, CD player for CDs, MD player for MDs, VCR for videotapes, LD player for LDs, DVD player for DVDs, personal computer for computer diskettes, etc.). In addition, the reproducing means can either be separate and distinct from treadmill 10 (as reflected in FIGS. 5 and 6) or, alternatively, the reproducing means can be integrated into treadmill 10 itself (as reflected in FIG. 7). The advantage with the former is that it enables treadmill 10 to interface and operate with existing audio and/or video components (e.g., televisions, home stereos, computers, etc.) that may already be found in the home and does not significantly increase the cost of treadmill 10.

The present invention also includes means, responsive to the control signals, for controlling the operation of treadmill 10. Where the reproducing means is separate and distinct from treadmill 10 (FIGS. 5 and 6), the control means comprises sensor means for sensing and converting the audio portion of the reproduced programming to an electrical signal, means for decoding said control signals, and means for driving said one or more motors or other electrically driven actuators in response to the decoded control signal. In one presently preferred embodiment, the sensor means is preferably a condenser microphone incorporated into the control panel 12 of treadmill 10. As the programming is reproduced by the reproducing means, the condenser microphone picks up the audio portion of the programming and converts or transforms the audio portion of the programming back into an electric signal. The output of the microphone is electrically coupled to decoder circuitry, which detects, separates out the control signals from the rest of the programming and interprets or decodes the control signals. The driving means, which is electrically coupled to the output of the decoder circuitry, drives the appropriate motors or actuators of treadmill 10 in response to the control signals received through the microphone as part of the programming. For example, when the tempo of the motivational content increases, the programming will contain a control signal to increase the speed of main motor 26 which, in turn, increases the speed of belt 36. As discussed in more detail below, the control signals are superimposed on the audio signal of the motivational content and are picked up by the microphone. The decoder circuitry then distinguishes between the control signal and the audio portion of the motivational content (i.e., dialog, sound effects, music), interprets the control signals and then provides the appropriate control signals to the appropriate motor or actuator of treadmill 10. Where the reproducing means is integrated into treadmill 10 (FIG. 7), a sensor means or microphone is not required. Instead, the output of the reproducing means is directly, electrically coupled to the decoder circuitry.

The presently preferred format for encoding the control signals will now be discussed. It should again be understood that the method of encoding set forth below is representative only and is not intended to limit the scope of this invention. Any number of encoding schemes, which are known to those skilled in the art, could be used to carry out, and are encompassed within, the scope of the present invention. In one presently preferred embodiment, the control signals are carried on a 2 kHz carrier signal, with each control signal consisting of two transmission bursts, each burst having three bytes of data. The second burst is intended to exactly duplicate the first burst for error checking purposes. The first byte of data of each burst indicates the desired speed of the treadmill, the second byte of data indicates the desired inclination of the tread base 16, and the third byte is a checksum of the first and second bytes. The control signals also preferably use standard RS232 protocol. Each control signal, including both bursts, is typically less than one-quarter second in duration. Each byte consists of 8 bits of data, giving a high degree of resolution for controlling treadmill speed and the degree of inclination. In one presently preferred embodiment, each time a control signal is inserted into the programming, the control signal entirely suppresses the audio portion of the motivational content for the duration of the control signal. As a result, the control signals are audible to the user, which also provides an audible cue or warning to the user that one or more operating parameters of treadmill 10 is about to change.

As alluded to above, the control signals are detected and decoded by a control signal decoder, which verifies that the control signal has the proper 2 kHz carrier frequency, checks to make sure that the control signal is otherwise properly formatted, and checks for errors. The decoder then passes the appropriate control signals to the processor, which in turn controls the appropriate operating parameters of the treadmill.

Figure 5:
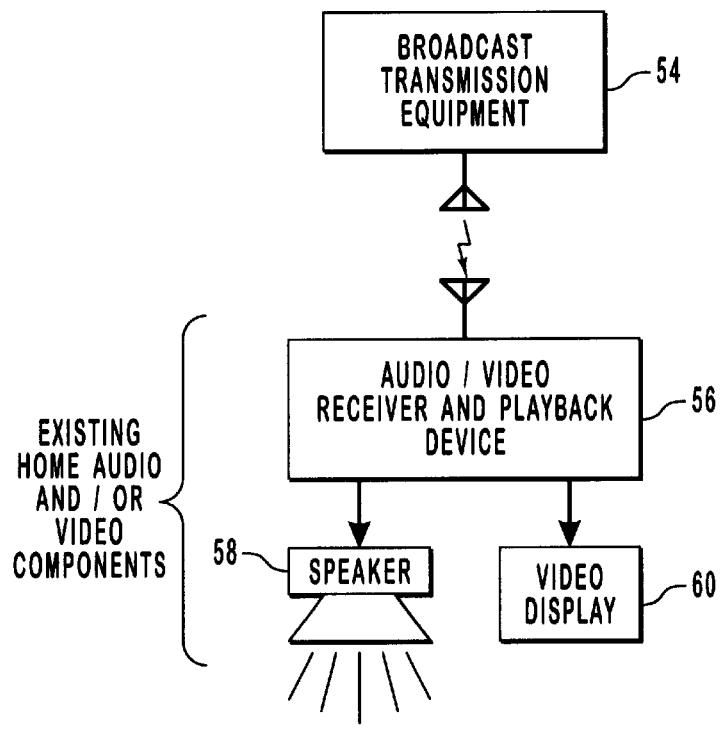
FIG. 5 is a functional block diagram of one presently preferred embodiment of the present invention.
Figure 5:
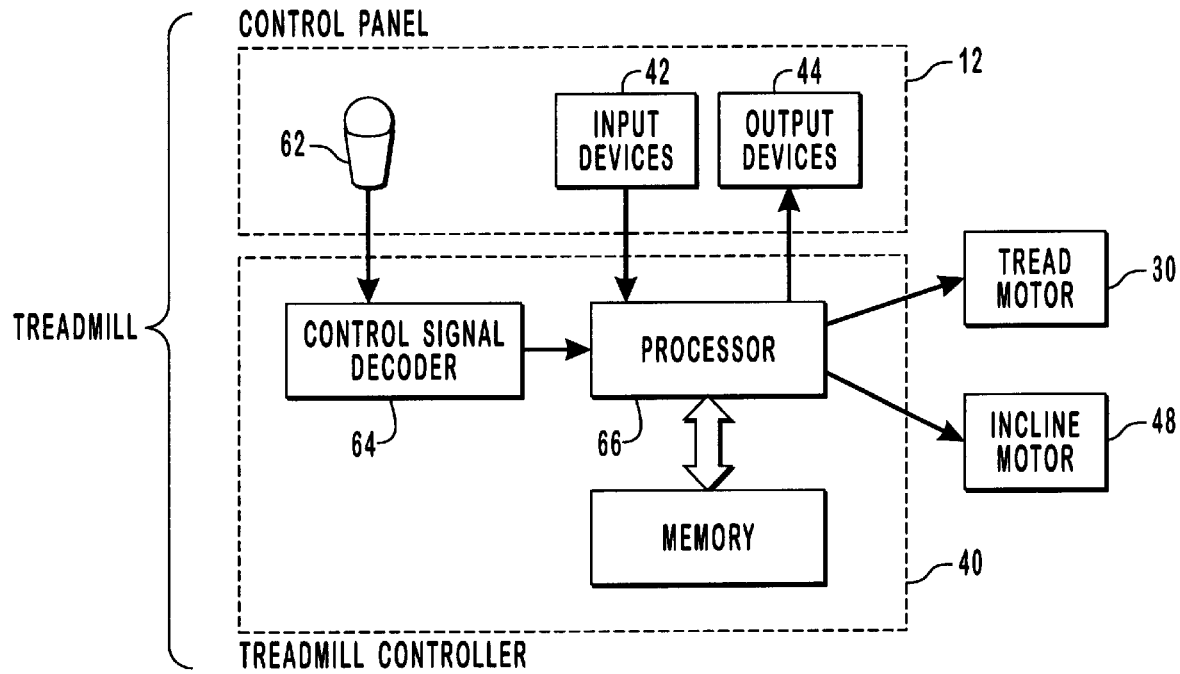

Reference is now made to FIG. 5, which is a functional block diagram of one presently preferred embodiment of the invention, wherein the programming is transmitted from a location remote from the treadmill 10. As alluded to above, the invention comprises means for reproducing the programming and means responsive to control signals encoded in the programming for controlling one or more operating parameters of treadmill 10 in synchronization with the motivational content of the programming. In the embodiment illustrated in FIG. 5, the structure corresponding to the reproducing means consists of conventional broadcast transmission equipment 54 in combination with a conventional audio and/or video receiver and playback device 56. Where, for example, the programming is transmitted via a television signal, receiver and playback device 56 may comprise a conventional television. Where the programming is transmitted via a radio signal, receiver and playback device 56 may comprise a conventional radio or home stereo receiver. In any event, the audio portion of the programming is reproduced by receiver and playback device 56 through a speaker 58. The video portion, if any, of the programming is displayed by receiver and playback device 56 through a suitable video display 60, such as a CRT, LCD or other similar device suitable for displaying video.

The invention also comprises means, responsive to control signals encoded in the programming, for controlling one or more operating parameters of treadmill 10 in synchronization with the motivational content of the programming, which comprises (i) sensor means for sensing and converting the audio portion of the reproduced programming into an electrical signal, (ii) means for decoding the control signals, and (iii) means for driving one or more operating parameters of the exercise device in response to the decoded control signals. In the embodiment illustrated in FIG. 5, the structure corresponding the sensor means comprises a microphone 62, which is integrated into the treadmills 10, preferably as part of the control panel 12. Microphone 62 receives the reproduced programming in the form of acoustic sound waves produced by speaker 58 and converts the received acoustic signals into an electric signal. The output of microphone 62 is received by control signal decoder circuit 64, which comprises the means for decoding the control signals. As discussed previously, decoder circuit 64 detects and identifies properly formatted control signals by checking for the proper 2 kHz carrier frequency and checking for errors by comparing the values of the first two bytes against the checksum contained in the third byte. Once decoder circuit confirms that a properly formatted control signal has been received, it then breaks down the control signal and separates out the speed control portion contained in the first byte from the inclination control portion contained in the second byte and passes the appropriate control signals to processor 66, which in turn adjusts the speed of tread motor 30 and/or the position of inclination motor 48 as dictated by the received control signal.

Figure 6:
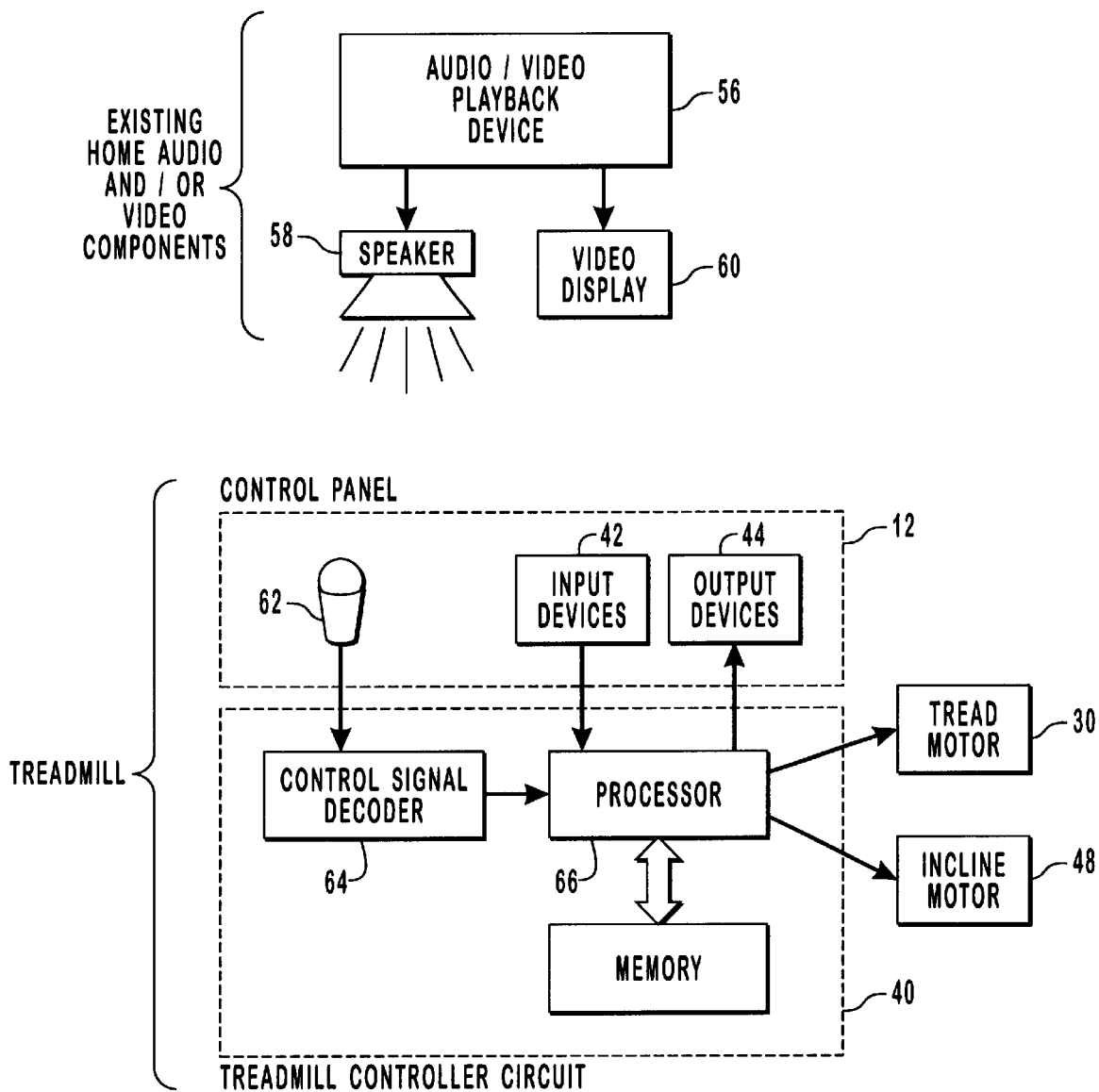
FIG. 6 is a functional block diagram of another presently preferred embodiment of the present invention.

Reference is now made to FIG. 6, which is a functional block diagram illustrating another presently preferred embodiment of the invention. The embodiment of FIG. 6 differs from that illustrated in FIG. 5 only in that it is intended to be used with programming that is stored on a player-readable storage medium, as opposed to be transmitted from a remote location via conventional broadcast channels. In this embodiment, the playback device 56 is selected based on the type of storage media on which the programming is recorded or otherwise stored. In all other material respects, the embodiment illustrated in FIG. 6 functions essentially the same as the embodiment illustrated in FIG. 5.

While the embodiments illustrated in FIGS. 5 and 6 both contemplate the use of a speaker and microphone as the presently preferred means of transferring the audio portion of the programming between receiver and playback device 56 and treadmill 10, it should be understood that other devices could readily be used to perform the same function. For example, an RF transmitter connected to receiver and playback device 56 and a compatible RF receiver connected to treadmill 10 could be used in place of speaker 58 and microphone 62. Similarly, an infrared transmitter and compatible infrared receiver could also be used to accomplish the same function.

Figure 7:
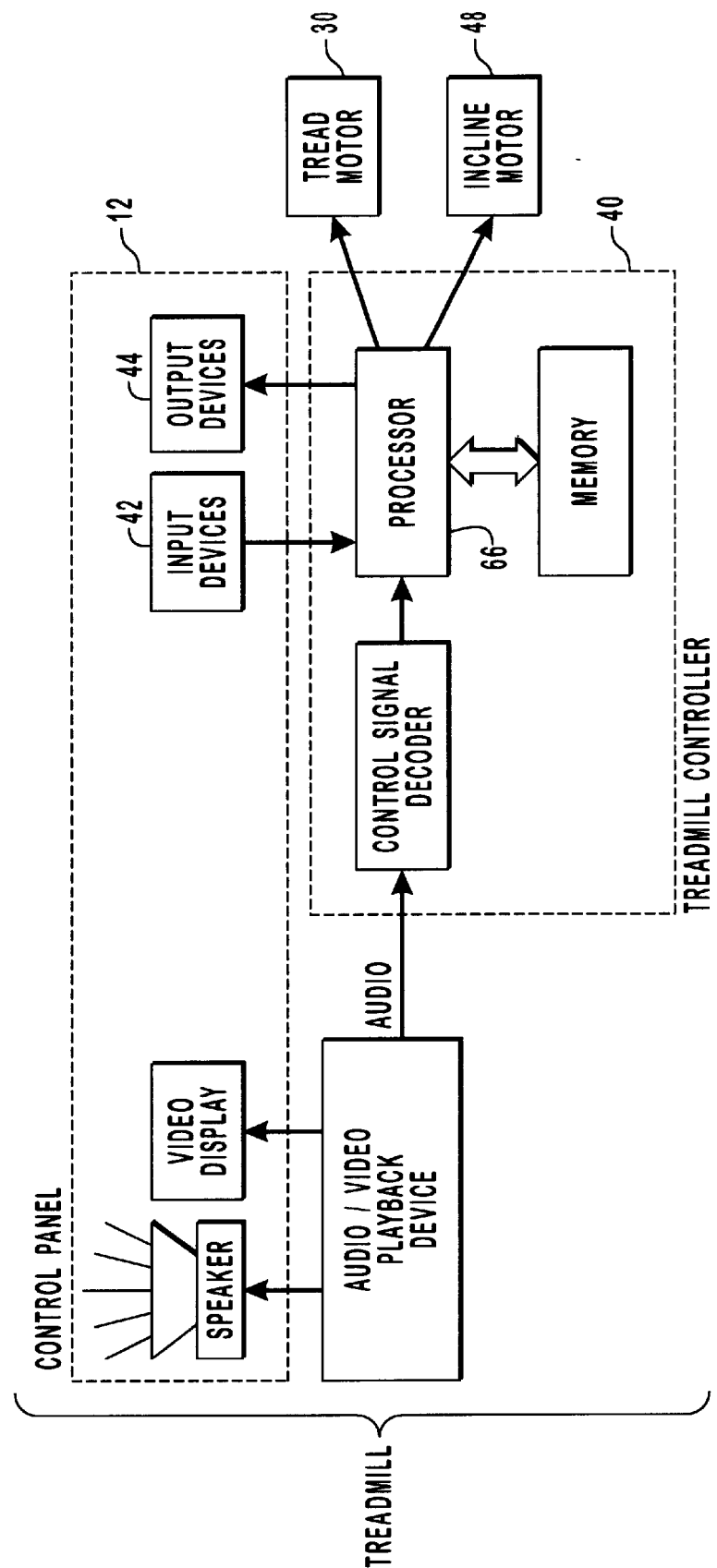
FIG. 7 is a functional block diagram of yet another presently preferred embodiment of the present invention.

Referring now to FIG. 7, which is a functional block diagram of yet another presently preferred embodiment of the invention. In this embodiment, playback device 56 is incorporated into treadmill 10, thereby eliminating the need for separate audio and/or video equipment. Where in the programming comprises only audio, playback device 56 preferably comprises an audio cassette player, a CD player, a MD player or other suitable audio playback device that is compatible with the format on which the programming is recorded or otherwise stored. Similarly, if the programming includes both audio and video, playback device 56 preferably comprises a display suitable for displaying video images in combination with either a video cassette player, a DVD player or a LD player. Preferably, the speakers 58 and/or video display 60 of the playback device 56 are incorporated into control panel 12 of treadmill 10.

The embodiment illustrated in FIG. 7 differs from the embodiments illustrated in FIGS. 5 and 6 in that it does not require the use of a separate sensor for sensing and converting the reproduced audio portion of the programming. Rather, the output of playback device is coupled not only to speaker 58 and/or video display 60, but is also electrically coupled to the input of control signal decoder circuit 64. In all other material respects, the embodiment illustrated in FIG. 7 functions essentially the same as the embodiment illustrated in FIG. 5.

Yet another embodiment of the present invention facilitates true interactive communications between a user, operating an exercise device in his or her own home, and a trainer or coach located at a remote location, wherein the trainer or coach can observe the user and control the user's exercise device remotely. In this embodiment, the exercise device incorporates a microphone, a video camera, a processor means, and a communications module, such as a modem. At the user's location, audio data is captured by the microphone and video data is captured by the video camera, which is then processed by the processor means by known methods. The exercise device is also preferably equipped with various sensors that detect the operating parameters of the exercise device, such as belt speed, degree of inclination, etc., and from which outputs are derived that are indicative of the present operating state of the exercise device at any given point in time. The audio, video and operating parameter data is then transmitted to the remote location for reproduction, viewing and monitoring by the trainer/coach at the remote location with minimal delays. In this embodiment, the preferred data transmission medium is a telephone line and a global computer network, such as the Internet. The invention is, however, not limited to the specific transmission medium, but may easily be adapted to other transmission media.

Similarly, audio and video data of the trainer/coach is captured and processed at the remote location and transmitted to the user for reproduction and viewing by the user with minimal delays. In addition, the trainer/coach is able to transmit control signals, encoded in the manner discussed above, to control, in real time, various operating parameters of the user's exercise device. In this manner, the exercise device of the present invention facilitates true interactive communications between a user exercising in his or her own home and a trainer/coach located in a remote location and control of the exercise device by the trainer/coach from the remote location.

The present invention is also directed to improved methods of operating an exercise device consistent with the teachings set forth above. In accordance with the present invention, the method includes the steps of (i) producing programming having motivational content and one or more control signals for controlling one or more parameters of an exercise device, (ii) transmitting the programming from a location remote from the exercise device; (iii) receiving and reproducing the transmitted programming; (iv) decoding the control signals, and (v) adjusting operating parameters of the exercise device in response to the decoded control signals such that the operation of the exercise device is synchronized with said motivation content. The actions corresponding to each of the foregoing steps are the same as and consistent with the teachings directed to apparatus discussed in detail above.

From the foregoing description, it will be apparent that the present invention provides advantages and features not previously found in the prior art. For example, the present invention provides exercise devices that incorporate a standardized interface for receiving and decoding control signals embedded in multimedia programming for controlling various operating parameters of the exercise device in synchronization with the multimedia programming. In addition, the present invention provides home exercise devices that are capable of simulating a group or class workout environment and synchronizing operation of the exercises devices with motivational programming. The present invention also provides improved exercise devices, wherein programming containing motivational content and control signals can be reproduced using audio and/or video playback devices commonly found in the home, such as televisions, VCRs, home stereo equipment and the like, and the exercise device can decode and utilize the control signals to synchronize operation of the exercise device with the motivational content. The present invention facilitates the use of interchangeable, multimedia programming that is external to the exercise device itself, making it possible to quickly and easily "program" the exercise device to perform an endless variety of exercise routines, accompanied by motivational content which is limited only be the imagination of producers of multimedia programming. The present invention also provides flexibility, in that the multimedia programming may be broadcast, either live or at a later time, from a location remote from the location of the exercise device or, alternatively, the multimedia programming can be recorded and/or stored on a suitable storage medium and reproduced at the convenience of the user. The present invention also facilitates live, interactive communications between a treadmill user at home and a trainer or coach in a remote location, which allows the trainer or coach to control the operating parameters of the user's treadmill on a live, real time basis.

Although preferred embodiments of the invention are described herein in detail, it will be understood by those skilled in the art that variations may be made thereto without departing from the spirit of the invention or the scope of the claims.

What is claimed and desired to be secured by United States Letters Patent is:

1. A data signal having data encoded thereon transmitted over a communication channel, comprising:
    (a) a first data field defining a first operating parameter value for one of one or more operating parameters of an exercise device;
    (b) a second data field defining a second operating parameter value for another of said one or more operating parameters of the exercise device; and
    (c) a third data field defining a checksum of said first byte of data and said second byte of data, said checksum configured to be used by the exercise device for error detection of the first operating parameter value and the second operating parameter value.

2. A data signal as recited in claim 1, wherein at least one of the first operating parameter value and the second operating parameter value indicates a speed of the exercise device.

3. A data signal as recited in claim 1, wherein at least one of the first operating parameter value and the second operating parameter value indicates an inclination of the exercise device.

4. A data signal as recited in claim 1, wherein at least one of the first operating parameter value and the second operating parameter value indicates a resistance of the exercise device.

5. A data signal as recited in claim 1, wherein the control signal comprise two transmission bursts.

6. A data signal as recited in claim 5, wherein said two transmission bursts are substantially identical.

7. A data signal as recited in claim 1, wherein at least one of said first byte, said second byte, and said third byte comprises at least eight bits of data.

8. A data signal as recited in claim 1, wherein said control signal is carried on a carrier signal to the exercise device.

9. A data signal as recited in claim 8, wherein the carrier signal has a frequency of 2 kHz.

10. A data signal as recited in claim 1, wherein the control signal is combined with motivational content and delivered to the exercise device.

11. A data signal as recited in claim 1, the control signal acting as an audible warning to a user of the exercise device of a change in said one or more operating parameters of the exercise device.

12. An improved exercise device having one or more motors or other electrically driven actuators for controlling one or more operating parameters of said exercise device, the improved exercise device comprising:
    programming having motivational content and at least two bursts of one or more control signals for controlling said one or more operating parameters of said exercise device, said motivational content including an audio portion;
    means for reproducing said programming, including said audio portion of said motivational content and said one or more control signals, said one or more control signals substantially suppressing said audio portion upon said means reproducing said one or more control signals; and means, responsive to said one or more control signals, for controlling said operating parameters of said exercise device in synchronization with said motivational content.

13. The improved exercise device of claim 12, wherein each of said one or more control signals comprises and each of said one or more control signals comprising:
   a first byte of data indicating a first operating parameter value for one of one or more operating parameters of the exercise device;
   a second byte of data indicating a second operating parameter value for another of said one or more operating parameters of the exercise device; and
   a third byte of data indicating a checksum of said first byte of data and said second byte of data.

14. The improved exercise device of claim 13, wherein each of the at least two bursts is substantially identical.

15. The improved exercise device of claim 12, wherein said one or more operation parameters comprising at least one of speed, inclination, and resistance.

16. The improved exercise device of claim 12, wherein the improved exercise device is a treadmill, the treadmill including a tread base and a belt.

17. The improved exercise device of claim 12, wherein each of said one or more control signals has a duration of less than one-quarter second.

18. The improved exercise device of claim 12, wherein said one or more control signals are carried by a carrier signal.

19. The improved exercise device of claim 12, wherein each of said one or more control signals acts as an audible cue to a change in said one or more operating parameters.

20. The improved exercise device of claim 12, wherein the programming is a television broadcast, a radio broadcast, a live broadcast, or a prerecorded broadcast.

21. The improved exercise device of claim 20, wherein the broadcast is transmitted by a transmission medium, the transmission medium is over the air waves, via cable, via satellite, or via the internet.

22. The improved exercise device of claim 12, wherein the programming is stored in nonvolatile memory.

23. The improved exercise device of claim 12, wherein the programming is prerecorded and stored on a storage medium.

24. The improved exercise device of claim 12, wherein said one or more control signals are synchronized with said motivational content.

25. The improved exercise device of claim 12, wherein said means for reproducing the programming is integrated into said exercise device.

26. The improved exercise device of claim 12, wherein said means for reproducing the programming is separate from said exercise device.

27. The improved exercise device of claim 12, wherein said controlling means comprises:
   means for decoding said control signals having an input and an output, the input of said decoding means being electrically coupled to the output of said reproducing means; and
   means, electrically coupled to the output of said decoding means, for driving said one or more motors or other electrically driven actuators in response to the decoded control signal.

28. The improved exercise device of claim 27, wherein said controlling means comprises:
   sensor means for sensing and converting the audio portion of the reproduced programming to an electrical signal, the sensor means having an output for outputting said electrical signal;
   means for decoding said control signals having an input and an output, the input of said decoding means being electrically coupled to the output of said sensing means; and
   means, electrically coupled to the output of said decoding means, for driving said one or more motors or other electrically driven actuators in response to the decoded control signal.

29. The improved exercise device of claim 12, wherein said reproducing means comprises a loudspeaker, an RF transmitter, or an infrared transmitter.

30. The improved exercise device of claim 29, wherein said sensor means comprises a microphone, an RF receiver, or an infrared receiver.

31. An improved exercise device having one or more motors or other electrically driven actuators for controlling one or more operating parameters of said exercise device, the improved exercise device comprising:
   programming having motivational content and one or more control signals synchronized with said one or more control signals for controlling said one or more operating parameters of said exercise device, said one or more control signals comprising at least two transmission bursts;
   means for reproducing said programming; and
   means, responsive to said one or more control signals, for controlling said operating parameters of said exercise device in synchronization with said motivational content.

32. The improved exercise device of claim 31, wherein the motivational content comprises an audio portion and a video portion.

33. The improved exercise device of claim 32, wherein said one or more control signals substantially suppressing said audio portion upon said means reproducing said one or more control signals.

34. The improved exercise device of claim 31, wherein said one or more control signals are carried in a 2 kHz carrier signal.

35. The improved exercise device of claim 31, wherein each of the at least two bursts is substantially identical.

36. The improved exercise device of claim 31, wherein each of said one or more control signals comprises a byte of data indicating a value of said one or more operating parameters.

37. The improved exercise device of claim 31, wherein each of said one or more control signals comprises:
   (a) a first byte of data indicating a selected speed of the exercise device;
   (b) a second byte of data indicating a selected inclination of the exercise device; and
   (c) a third byte of data indicating a checksum of said first byte of data and said second byte of data.

38. The improved exercise device of claim 31, wherein said one or more control signals use a RS232 protocol.

39. A method of operating an exercise device having one or more motors or other electrically driven actuators for controlling one or more operating parameters of said exercise device, the method comprising:
   a step for receiving programming having motivational content and two bursts of one or more control signals configured to control one or more operating parameters of the exercise device, said motivational content comprising an audio portion synchronized with said one or more control signals;

a step for reproducing the received programming, including said audio portion of said motivational content and said one or more control signals, said one or more control signals substantially suppressing said audio portion of said motivational content; and upon decoding said one or more control signals, a step for adjusting said one or more operating parameters of said exercise device in response to said decoded control signals.

40. The method of claim 39, further comprising transmitting said motivational content and said one or more control signals to the exercise device.

41. The method of claim 40, wherein the transmitting step comprises broadcasting said programming over air waves, broadcasting said programming via cable, broadcasting said programming via satellite, or broadcasting said programming over the internet.

42. The method of claim 39, further comprising identifying a first byte of data, a second byte of data, and a third byte of data included in each of said one or more control signals.

43. The method of claim 42, further comprising comparing said third byte of data against said first byte of data and said second byte of data to detect errors.

44. The method of claim 39, further comprising comparing said one or more control signals contained in a first burst of said two bursts against said one or more control signals contained in a second burst of said two bursts.

45. The method of claim 39, wherein said one or more control signals comprises at least one speed signal and at least one incline signal.

* * * * *

UNITED STATES PATENT AND TRADEMARK OFFICE
CERTIFICATE OF CORRECTION

PATENT NO. : 6,626,799 B2
DATED : September 30, 2003
INVENTOR(S) : Scott R. Watterson, William T. Dalebout and Darren Ashby It is certified that error appears in the above-identified patent and that said Letters Patent is hereby corrected as shown below:

Title page,
Item [56], References Cited, U.S. PATENT DOCUMENTS, change "sweat equity" to -- sweat.equity --; change "6/2003" to -- 1/2003 --; and change "Babbitt" to -- Babbit -- FOREIGN PATENT DOCUMENTS, insert
-- WO 98/32496   7/1998   PCT ……... A63B/B65G --;
Item [57], ABSTRACT,
Line 9, after "in" delete "a"

Column 4,
Line 11, delete "which"
Line 12, delete "depict"
Line 12, after "10" insert -- is shown --
Line 43, before "portion" insert -- a --

Column 9,
Line 30, delete "motivation" and insert -- motivational --

Column 10,
Line 36, delete "comprise" and insert -- comprises --

Column 11,
Line 6, delete "and each"
Line 7, delete "of said one or more control signals comprising"
Line 18, delete "operation" and insert -- operational --

UNITED STATES PATENT AND TRADEMARK OFFICE
CERTIFICATE OF CORRECTION

PATENT NO.    : 6,626,799 B2
DATED         : September 30, 2003
INVENTOR(S)   : Scott R. Watterson, William T. Dalebout and Darren Ashby It is certified that error appears in the above-identified patent and that said Letters Patent is hereby corrected as shown below:

<u>Column 12,</u>
Line 36, delete "suppressing" and insert -- suppresses --

Signed and Sealed this

Twentieth Day of April, 2004

JON W. DUDAS
*Acting Director of the United States Patent and Trademark Office*